United States Patent [19]

Katz

[11] 4,388,441

[45] Jun. 14, 1983

[54] INDUCTION OF IMMUNOLOGICAL TOLERANCE

[75] Inventor: David H. Katz, La Jolla, Calif.

[73] Assignee: Scripps Clinic & Research Foundation, La Jolla, Calif.

[21] Appl. No.: 937,574

[22] Filed: Aug. 28, 1978

Related U.S. Application Data

[62] Division of Ser. No. 764,586, Feb. 3, 1977, Pat. No. 4,191,668.

[51] Int. Cl.$^3$ .................... C08G 69/48; C08G 69/50
[52] U.S. Cl. .................... 525/54.1; 424/78; 424/85; 424/88; 525/420; 528/310
[58] Field of Search ........... 528/328, 311; 424/78, 424/88, 85; 525/54.1, 420

[56] References Cited

U.S. PATENT DOCUMENTS 3,794,630  2/1974  Mullan et al. ................ 260/112 R

OTHER PUBLICATIONS

Noss et al., *J. of Expl. Med.*, vol. 138, (1973), pp. 312–317.
Eshhar et al., *J. Immunol.*, vol. 114, No. 2, (1975), pp. 872–876.
Chiorazzi et al., *Proc. Natl. Acad. Sci. U.S.A.*, vol. 73, No. 6, Jun. 1976, pp. 2091–2095.
Bitter–Suermann et al., *Chemical Abstracts*, vol. 83, 129,895p, (1975).
Mosier et al., *Chemical Abstracts*, vol. 83, 191,237d, (1975).

*Primary Examiner*—Howard E. Schain
*Attorney, Agent, or Firm*—Hubbard & Stetina

[57] ABSTRACT

Immunosuppressive agents which are conjugates of an antigen linked to a D glutamic acid:D-lysine copolymer are disclosed. Also disclosed are methods of preparing the conjugates and therapeutic methods for inducing immunological tolerance to antigens.

4 Claims, No Drawings

INDUCTION OF IMMUNOLOGICAL TOLERANCE

This is a division of Ser. No. 764,586, filed Feb. 3, 1977, now U.S. Pat. No. 4,191,668.

BACKGROUND OF THE INVENTION

1. Field of the Invention

The present invention relates to conjugates suitable for inducing in an individual immunological tolerance to an antigen. The conjugates function by suppressing the formation of antibodies to a specific antigen. Antigens can be defined as macromolecules which will, when introduced into an individual, cause the production of antibodies by that individual and will react specifically with those antibodies.

The basic function of the organs, cells and molecules that comprise the immune system is to recognize and to eliminate from the body foreign substances. These foreign substances are eliminated by reaction between the foreign substance and antibodies which are formed in response to the substance. In general, this function is performed efficiently and without detriment to the host. However, in certain instances, disturbances can occur which can lead to pathogenic disorders such as, for example, an uncontrolled response (allergic disorders) or an abnormal response (autoimmune disease). The pathogenesis of both these disorders is related directly or indirectly to the production of antibodies to either environmental antigens (allergens) or self-antigens. In addition, since the function of the immune system is to recognize and eliminate foreign substances, transplantation of healthy tissue and organs from a donor to a genetically non identical (i.e., allogenic) acceptor individual is difficult to achieve because of the allograft reaction.

If an individual undergoes an "altered state" as a result of contact with an antigen (and formation of antibodies thereto), subsequent contact with that antigen or a structurally similar substance can evoke a pathological reaction. Such individuals are termed "hypersensitive", with regard to one or more specific reaction provoking antigens. When these individuals inhale or ingest the appropriate antigen, a prominent and common manifestation includes hayfever, asthma or hives. The tendency to develop this form of allergy ("atopy") is hereditable.

An individuals first antibody response to an antigen evokes a smaller and somewhat different antibody response that the response evoked upon subsequent exposure. The first exposure to an antigen evokes a primary response. After antibody levels in the primary response have declined, even to the point of no longer being detectable, a subsequent encounter with the same antigen usually evokes an enhanced secondary (anamnestic) response.

The appearance of this atopy is involved with the production within an individual of a type of tissue-sensitizing IgE antibody called a reagin. These IgE antibodies have a high affinity for receptors or cells present in various body tissues. The receptors are on mast cells which are found in close association with capillaries in connective tissues throughout the body and on basophilic leukocytes (blood cells). Mast cells and basophils contain a high content of pharmacologically-active mediators, such as histamine, serotonin, (5-hydroxytryptamine) and kinins (basic peptides), concentrated in cytoplasmic granules. Contact of the IgE antibodies, which are fixed to mast cells and basophils, with antigens can trigger cross-linking of the IgE antibodies. In turn, this cross-linking causes degranulation of mast cells and basophils, which releases the chemical mediators and produces manifestations of the allergic response referred to earlier.

While the appearance of atopy is dependent upon production of cell-bound (IgE) antibodies, another type of antibodies of importance to the immune system is of the IgG class. These IgG antibodies are referred to as circulating antibodies or "blocking" antibodies. IgG antibodies are also capable of combining with antigens. This combination can inactivate antigens by "blocking" the ability of the antigen to react with cell bound IgE, and subsequent crosslinking of the IgE antibodies.

A common method of treating allergic disorders is by immunizing ("desensitizing") the individual by repeated injections of small, increasing amounts of antigen, at intervals, e.g., weekly, and at dosage levels that avoid triggering of the degranulation of mast cells or basophils. It is believed that repeated injections increase the level of blocking IgG antibodies, but not the level of cell-bound IgE antibodies.

This desensitizing approach is subject to a number of disadvantages. Therapeutic benefits are difficult to achieve consistently, and the treatment is tedious. In addition, since exposure to the environmental antigen causes subsequent production of IgE antibodies, the possibility of an IgE-antigen reaction and subsequent IgE cross-linking, is always present.

An autoimmune disease is a pathological condition arising from an autoimmune response in which an individual responds immunologically by production of antibodies to a self-antigen. Autoimmunity can affect almost every part of the body, and generally involves a reaction between a self-antigen and IgG antibody. Representative autoimmune diseases can involve the thyroid, gastric mucosa, adrenals, skin, red cells and synovial membranes.

For some types of autoimmune diseases, non-specific immunosuppressant treatment, such as whole body X-irradiation or the administration of cytotoxic drugs, has been used with limited success. The disadvantages of such treatment include the toxicity of the agents used, and the increased incidence of various cancers, especially lymphomas and reticulum cell sarcomas, following such therapy. In addition, the use of nonspecific agents for chronic immunosuppression greatly increases the susceptibility of the patient to serious infection from environmental fungi, bacteria and viruses which under ordinary circumstances would not cause problems. The invention disclosed herein is specific and only suppresses the antibody response to the offending antigen.

In contrast to the "blocking" desensitization approach of treatment of environmental allergies with antigen extracts, and the non-specific immunosuppression of autoimmune diseases, the present invention provides a means of inducing a long-lasting state of specific immunological tolerance by suppression of formation of antibodies to specific antigens.

2. Prior Art

In viewing the prior art in the field of immunology, it is important to recognize the distinction between an antigen and a hapten. As defined hereinbefore, antigens cause the production of antibodies and also react specifically with the antibody produced. In contrast, haptens are defined as a small molecule which by itself cannot stimulate antibody production, but will combine with an antibody, once formed. Further, haptens as a rule do not induce cellular immunity, cannot serve as carriers for other haptens and induce antibody formation only when introduced on immunogenic carriers. An antihapten antibody response has strict carrier specificity. A secondary response to the hapten can only be elicited when it is administered on the same carrier; if it is introduced on an immunologically unrelated carrier, an individual will shown no immunological memory for the hapten and will give a typical primary response.

Because the capacity for a secondary response can persist for many years it can provide a long-lasting immunity. The primary response is less protective, because antibodies appear more slowly. In a series of papers one of the inventors and his co-workers demonstrated and characterized a system of prolonged hapten-specific bone-marrow derived cell tolerance using the D-glutamic acid:D-lysine copolymer to which the appropriate hapten had been attached. [See *J. Exp. Med.*, Vol. 134, pp. 201–223 (1971); Vol. 136, pp. 1404–1429 and pp. 426–438 (1972); Vol. 138, pp. 312–317 (1973); Vol. 139, pp. 1446–1463 (1974) and *Proc. Natl Acad. Sci.* U.S.A. Vol. 71, pp. 3111–3114].

These studies demonstrated success in inducing tolerance in the bone-marrow derived lymphocyte precursors of antibody forming cells of antibody classes which were specific for the 2,4 dinitrophenyl (Dnp) hapten. The investigations involved the use of conjugates of Dnp and D-glutamic acid:D-lysine, (hereinafter D-GL).

Recent studies by one of the inventors and co-workers demonstrated that tolerance to nucleoside determinants could be obtained by using conjugates of nucleosides and D-GL. [See *J. Immunol.*, Vol. 114, pp. 872–876 (1975)]. The nucleoside work dealt with the induction of tolerance to a mixture of nucleosides, which are made up of a heterocyclic base and a five-carbon sugar. This work is similar to induction of tolerance to DNP-D-GL.

While these immunological studies are of interest in demonstrating suppression of antibody response to chemical moieties which function as single determinants when coupled to appropriate non-immunogenic carriers such as D-GL copolymer, no immunotherapeutic application to antigens is disclosed.

The experimental results herein which relate to penicillin allergy, and the use of the major antigenic determinant, benzylpenicilloyl (BPO), are described in *Proc. Natl. Acad. Sci.* U.S.A., Vol. 73, No. 6. pp. 2091–2095 (1976).

SUMMARY

The subject matter of the present invention includes:
(a) a therapeutic immunosuppressive agent capable of suppressing specific antibody formation in an individual. The agent is a conjugate of D-glutamic:D-lysine copolymer and an antigen. The antigen can be either an allergen or a self-antigen. Allergens include: benzylpenicilloyl, insulin, ovalbumin, lactalbumin, bermuda grass pollen, timothy grass pollen, orchard grass pollen, and combinations of grass pollen, ragweed pollen, ragweed antigen E, birch tree pollen, bee venom, snake venom, horse dander, cat epithelial, haddock, house dust mite, *Chrysanthemum leucanthemum*, *Alternaria tenuis*, trypsin, chymotrypsin, dry rot, baker's yeast, tetanus toxoid, diphtheria toxin, ficin and derivatives thereof. Self-antigens include: nuclei acid, oligodeoxynucleotide, thyroglobulin, thyroid cell surface or cytoplasm, parietal cell, adrenal cell, epidermal cell, uvea cell, basement membrane cell, red cell surface, platelet cell surface, muscle cell, thymus myoid cell, mitochondria, secretory duct cell, deoxyribonucleic acid-protein, acetylcholine receptor substance, insulin and other normal hormone and tissue factors.

(b) a method for preparing a therapeutic immunosuppressive agent by reacting a D-glutamic acid:D-lysine copolymer with an antigen. The coupled antigen-D-GL conjugate is recovered by conventional purification techniques; and (c) a therapeutic method of inducing immunological tolerance to an antigen in an individual for whom such therapy is indicated, by administration of a conjugate of antigen and D-glutamic:D-lysine copolymer, as defined above.

DESCRIPTION OF THE INVENTION

The present invention relates to induction of immunological tolerance to specific offending antigens. The antigen is coupled to a D-GL copolymer. The immunological tolerance achieved can be defined as a specific unresponsive state in which the individual fails to form antibodies, in response to the introduction into the individual, of the antigen. The tolerance induced was manifested by:

(1) the inability of an individual treated with antigen-D-GL to develop primary antigen-specific antibody responses;

(2) the ability of antigen-D-GL conjugate to abrogate an ongoing anti-antigen antibody response; and (3) the inability of an individual previously primed with an antigen to generate secondary anti-antigen responses following treatment with antigen-D-GL conjugate.

The suppression is accomplished by administering to that individual an amount of the antigen-D-GL conjugate that has an effective suppressing effect upon specific antibody response. The term "individual" as utilized in this specification means a human being or an experimental animal that is a model for a human being. Medical indications for the use of the conjugate of the present invention are any conditions in which it is desired to suppress within the individual antibody response to a specific antigen. The term "suppression of antibody response" or any equivalent of that term means a significant increase in immunological tolerance to a specific antigen. This suppression is accomplished by administering to the individual a dose, or series of doses, which will suppress or decrease antibody response. Although the amount will vary from individual to individual and from indication to indication, it is easily determined by one skilled in the art without undue experimentation. Subcutaneous administration is preferred. Dose forms for administration of the conjugate can be prepared by recognized methods in the pharmaceutical sciences.

Hypersensitivity reactions to drugs, such as penicillin, are a common allergic disorder in humans. The mechanisms involved which are illustrated with penicillin can be considered as models for allergies in general. In order to conduct a thorough investigation of suppression of specific antigen-antibody response, a penicillin model of allergy was used.

Penicillin is relatively unstable and most of its solutions contain at least small amounts of penicillinate, a highly reactive derivative that forms penicilloyl and other substituents of amino and sulfhydral groups of proteins. Penicillin G, derived from crystalline potassium benzylpenicillin G (KPG), the most widely used pencillin, has a benzyl group attached to the carboxyl group; the major antigenic determinant of penicillin G, that is, the restricted portion of the antigen molecule which determines the specificity of the antibody-antigen reaction, is benzylpenicilloyl (hereinafter BPO).

The process for producing the antigen D-GL conjugates of the present invention involves dissolving D-GL copolymer in an alkaline solution and reacting the alkaline solution with from about 2 to 3 molar equivalents of the antigen. The reaction mixture is maintained at a temperature of from about 10° to 30° C. for about one hour. The pH of the reaction mixture is maintained in a range of about 10-12, by addition of a alkaline material e.g., KOH or NaOH. The antigen conjugates are washed and purified by known techniques, e.g. dialysis. Suitable copolymers, having a molecular weight of about 34,000 about 50,000 and about 64,000, respectively, and a glutamic acid:lysine molar ratio of 60:40 are available from Miles Laboratories, Inc., 1127 Myrtle Street, Elkhart, Ind., 46514.

In order to determine the immunospecific characteristics of the conjugates of the present invention, high-titered IgE, IgG and IgM antibody responses to an antigen were elicited in mice by the intraperitoneal (i.p.) injection of an antigen keyhole limpet hemocyanin (KLH). The amount of antibody produced in response was then measured by the assay techniques described hereinafter. Treatment of such mice with the antigen-D-GL, according to the present invention, either before or after the primary immunization, resulted in significant suppression of the subsequent anti-antigen antibody response of the IgE and IgG classes, measured at both the humoral and cellular level.

ASSAY TECHNIQUES

I. BPO-Carrier Conjugates (a) BPO-KLH and BPO-BSA

BPO was coupled to keyhole limpet hemocyanin (KLH) and to bovine serum albumin (BSA) as described in *J. Clin. Invest.* 47, pp. 556-567 (1968) and *Int. Arch. Allergy*, 39, pp. 156-171 (1970). The protein concentration of the conjugates was determined by Kjeldahl nitrogen analysis (with a correction for the amount of nitrogen contributed by the BPO groups). The conjugates were assayed for BPO content by determining the penamaldate concentration. The penamaldate measurement involves spectrophotometric quantitative determination of the BPO-D-GL conjugate. [See *Methods in Immunology and Immunochemistry*, Academic Press, pp. 141-142 (1967)]. The molar ratio of BPO/KLH and BPO/BSA obtained was:

$BPO_{35}$-BSA (10 equivalents of potassium benzylpenicillin equivalent to $\Sigma$-$NH_2$);

$BPO_{10}$-KLH (10 equivalents of potassium benzylpenicillin equivalent to $\Sigma$-$NH_2$; molecular weight of subunit of KLH of 100,000, with estimated 50$\Sigma$-$NH_2$ groups).

(b) BPO-SRBC (Sheep Erythrocytes)

For use in testing serum BPO-specific IgM and IgG antibodies, BPO was coupled to SRBC by the method described in *J. Immunol.* 96, pp. 707-718 (1966).

The BPO-carrier conjugates, prepared as described above were utilized in immunization of mice or in measurement of anti-BPO antibodies as described in detail hereinafter.

II. Immunization Procedure

Mice were immunized by intraperitoneal (i.p.) injection of 1 μg of BPO-KLH adsorbed on 4 mg of Al-$(OH)_3$ gel (alum) in a volume of 0.5 ml sterile saline. Booster injections were given i.p. from 2 to 4 weeks after primary injections. Booster injections were made with 1 μg BPO-KLH mixed with 2 mg of alum.

At various intervals after primary and secondary immunization, mice were bled from the retro-orbital plexus and the serum antibody levels determined as described below.

III. Measurement of Anti-BPO Antibodies

Serum IgE antibodies.
Passive Cutaneous Anaphylaxis (PCA)

The PCA method involves pooling sera from a given group of mice and serially diluting (2-fold) the sera in 2 percent normal rat serum. A 0.1 ml portion of each of the various dilutions was injected intradermally into the shaven dorsal skin of the test rats. After a 4-24 hour sensitization period, the PCA reactions, which measure only IgE antibodies by this technique, were elicited by intravenous (i.v.) injection of BPO-BSA (1 mg/250 gm of shaved rat body wt) in 1.0 percent Evans' blue dye dissolved in phosphate-buffered saline. The PCA titer is expressed as the reciprocal of the highest dilution of serum yielding a 5 mm diameter blueing reaction. [See *Life Sciences*, 81, pp. 813-820 (1969)].

IV. Measurement of Serum Anti-KLH Antibodies

Serum IgE anti-KLH antibody levels were determined by PCA reactions as described above. IgG anti-KLH antibodies were determined by radioimmunoassay using $^{125}I$-labelled monomeric KLH as described in *J. Immunol.* 114, pp. 872-876 (1975).

DESCRIPTION OF THE PREFERRED EMBODIMENTS

The following examples illustrate preparation of the conjugates of the present invention.

EXAMPLE I

BPO-D-GL Conjugate

A one gram portion of D-GL copolymer having an average molecular weight of about 50,000, and a glutamic acid:lysine residue molar ratio of 60:40, was dissolved in 0.1 m sodium carbonate solution (pH=11.5). The pH was maintained at about 10-12 by additions of 1 NaOH. From 2 to 3 molar equivalents of potassium benzylpenicilloyl was added, and the reaction mixture maintained at a temperature of about 10° to 30° C. for about 1 hour.

The resultant BPO-D-GL conjugate was separated from the unreacted penicillin salt by dialysis purification. The dialysis involved several changes of 0.1 M sodium bicarbonate containing 1 percent diethylaminoethyl cellulose (DEAE), and finally against phosphate-buffered saline.

Analysis of the BPO-D-GL conjugate by the method referred to earlier indicated that the BPO-D-GL molar ratio was $BPO_{40}$-D-GL (2 equivalents potassium benzylpenicillin/equivalent $\Sigma$-$NH_2$). The BPO-D-GL conjugate formed has a molar ratio of benzylpenicilloyl, or a derivative thereof, to copolymer, of at least 40:1.

High titered IgE, IgG and IgM antibody responses to BPO were elicited by the i.p. injection of BPO-KLH. Treatment of such mice, as described hereinafter, with the BPO-D-GL according to the present invention, either before or after the primary immunization, resulted in significant suppression of the subsequent anti-BPO antibody response of the IgE and IgG classes, measured at both the humoral and cellular level.

Induction of BPO-Specific Tolerance With BPO-D-GL When BPO-D-GL Treatment Precedes Primary Immunization Analysis of Humoral Immune Responses.

Two groups of normal BALB/c mice were injected subcutaneously (s.c.) with four doses of either saline or 500 µg of BPO-D-GL at 3 day intervals. This regimen was chosen on the basis of preliminary experiments which demonstrated that: (1) the subcutaneous route is as good as or better than intraperitoneal for tolerance induction with D-GL conjugates, and (2) two 500 µg doses of BPO-D-GL resulted in a significant, but incomplete degree of tolerance. One week after the last dose, animals were primarily immunized with 1 µg of the sensitizing antigen BPO-KLH mixed with 4 mg of alum, an immunization procedure which was found to induce good IgE, IgM and IgG primary anti-BPO antibody responses in such mice. All animals were bled at weekly intervals and their sera analyzed for anti-BPO and anti-KLH antibodies. On day 28 after primary immunization, the mice in both groups were secondarily challenged with 1 µg of BPO-KLH mixed with 2 mg of alum; 7 days later they were bled and sacrificed. The protocol and data of serum antibody responses are summarized in Table I. Control animals developed good primary IgE anti-BPO antibody responses by day 14, which peaked by day 21; these animals manifested sharp anamnestic responses on day 35 following secondary challenge on day 28. In contrast, mice which had been pretreated with BPO-D-GL failed to produce detectable IgE anti-BPO responses over the 28 day primary course and produced only low amounts of antibody following secondary challenge. Comparable IgE anti-KLH antibody titers between treated and control mice over the 35 day observation period indicated tolerance specificity.

Serum BPO-specific IgM and IgG antibodies were determined by passive hemagglutination utilizing BPO coupled to sheep erythrocytes as described in *J. Immunol.* 111, pp. 638–640 (1973). The anti-BPO antibody responses of the IgG and IgM class were similar to the IgE class results described above. Mice treated with BPO-D-GL displayed significantly lower levels of IgG anti-BPO serum antibody over the entire immunization period and following secondary challenge as compared to controls.

Spleen cells were removed under sterile conditions, and analyzed for BPO-specific plaque forming cells by the technique described in *Science* 140, pp. 405–411 (1963). Heterologous adoptive cutaneous anaphylaxis reactions were performed as described in *J. Immunol.* 111, pp. 638–640 (1973). The data indicated that substantially fewer BPO-specific antibodies of the IgG and IgM classes were present in spleen cells of mice treated with BPO-D-GL as compared with untreated control mice.

TABLE I

Sera Antibody Response Effect of BPO-D-GL Pretreatment on Primary IgE Anti-BPO Antibody Responses of BALB/c Mice to BPO-KLH (PCA Titer)

| PROTOCOL | | | SERUM ANTI-BPO ANTIBODY IgE |
|---|---|---|---|
| Group | Pretreatment | Days After Priming | |
| I | (Control) Saline s.c. | 7 | <10 |
| | | 14 | 160 |
| | | 21 | 320 |
| | | 28 | 320 |
| | | 35 | 2560 |
| II | BPO-D-GL s.c. (500 µg × 4) | 7 | <10 |
| | | 14 | <10 |
| | | 21 | <10 |
| | | 28 | <10 |
| | | 35 | 40 |

Secondary challenge was administered on day 28.

Induction of BPO-Specific Tolerance in Previously Immunized Mice by Administration of BPO-D-GL Three groups of BALB/c mice were immunized i.p. with 1 µg of BPO-KLH mixed with 4 mg of alum. Two weeks later, the groups were bled and then treated with either saline, 500 µg of BPO-D-GL i.p. or 500 µg of BPO-D-GL s.c. on two alternating days (days 14 and 16). On day 18, all animals were secondarily challenged with 1 µg of BPO-KLH mixed with 2 mg of alum and bled at 7 day intervals over the ensuing 3 weeks. Twenty-one days after secondary immunization, the animals were sacrificed and their spleen cells assayed for BPO-specific plaque forming cells.

The protocol and data of serum antibody responses are summarized in Table II. All 3 groups of mice displayed comparable levels of IgE anti-BPO antibodies immediately preceding BPO-D-GL treatment. Following secondary challenge with BPO-KLH, the untreated control mice manifested anamnestic IgE responses which plateaued on days 7 and 14 and declined somewhat by day 21 after challenge. In contrast, the 2 groups treated with BPO-D-GL failed to respond to secondary immunization with BPO-KLH and, moreover, exhibited a decrease in circulating IgE anti-BPO antibody levels, this being most marked in the group treated with BPO-D-GL subcutaneously; the IgE titer in the latter group declined progressively until none was detectable by day 21. Comparable IgE anti-KLH antibody titers between treated and control mice over the 21 day observation period indicated tolerance specificity.

Similar findings in anti-BPO antibody responses of the IgG class were obtained. Thus, mice treated with BPO-D-GL were substantially suppressed in their IgG anti-BPO responses as compared to controls.

TABLE II

Effect of Intervening Treatment with BPO-D-GL On Secondary IgE Anti-BPO and Anti-KLH Antibody Responses of BALB/c Mice to BPO-KLH

| PROTOCOL | | | SERUM ANTI-BPO ANTIBODY (PCA TITER) IgE |
|---|---|---|---|
| Group | Intervening Treatment | Days After Secondary Challenge | |
| I | (Control) Saline | −4 | 320 |
| | | 7 | 1280 |
| | | 14 | 1280 |
| | | 21 | 300 |
| II | BPO-D-GL i.p. (500 µg × 2) | −4 | 320 |
| | | 7 | 40 |
| | | 14 | 40 |
| | | 21 | 40 |

TABLE II-continued

Effect of Intervening Treatment with BPO-D-GL
On Secondary IgE Anti-BPO and Anti-KLH
Antibody Responses of BALB/c Mice to BPO-KLH

| | PROTOCOL | | SERUM ANTI-BPO ANTIBODY (PCA TITER) IgE |
|---|---|---|---|
| Group | Intervening Treatment | Days After Secondary Challenge | |
| III | BPO-D-GL s.c. (500 μg × 2) | −4 | 320 |
| | | 7 | 40 |
| | | 14 | 20 |
| | | 21 | <10 |

Spleen cell tests indicated that the level of BPO-specific antibodies of the IgG and IgM class in the spleens of treated mice were lower than in the spleens of untreated controls.

From the above, it can be seen that the present invention provides a method whereby a state of immunological tolerance to a specific antigen can be induced in an individual by administration of the appropriate antigen-D-GL conjugate. The tolerance is manifested in the IgE as well as the IgG and IgM antibody class. In addition, the test results show that tolerance can be established irrespective of the immune status of the animal at the time of treatment.

EXAMPLE II

BPO-D-GL Conjugate

A one g portion of D-GL copolymer, having an average molecular weight of about 64,000 and a glutamic acid:lysine residue molar ratio of 60:40, and a 0.5 g portion of potassium benzylpenicilloyl were dissolved in 0.1 M sodium carbonate solution. The pH was kept between 10-12 by additions of 1 N NaOH. The reaction mixture was maintained at a temperature of about 30° C. for about 1½ hours.

The resultant BPO-D-GL conjugate was separated from unreacted penicillin salt by dialysis against 0.1 M NaHCO$_3$ containing 1 percent DEAE cellulose. Dialysis was allowed to proceed for a period of about one week.

Analysis of the BPO-D-GL conjugate obtained, by the method referred to earlier, indicated that the BPO:D-GL molar ratio was BPO$_{63}$-D-GL.

EXAMPLE III

Insulin—D-GL Conjugate

A 50 mg portion of porcine insulin was dissolved in 0.01 M ethylenediaminetetraacetic acid (EDTA) at a pH of 3.1. The dissolved insulin was dialyzed against the same EDTA solution overnight. The dialyzing medium was changed to 0.033 M borate buffer at a pH of about 9.5, containing $2.5 \times 10^{-5}$ M EDTA. Toluene-2,4-diisocyate (TDIC) was added to the insulin solution at 0° C. The reaction mixture was stirred vigorously at 0° for about 30 min. and then centrifuged at 12,000 g for 10 min. at a temperature of about 2° to 4° C. The supernatant was decanted into a stoppered test tube and the test tube placed in an ice bath. The reaction was allowed to proceed an additional hour at ice bath temperatures.

A 50 mg portion of D-GL copolymer having an average molecular weight of 64,000 and a glutamic acid:lysine molar ratio of 60:40, was dissolved in 0.033 M borate buffer (pH 9.5), containing $2.5 \times 10^{-5}$ M EDTA. The pH was adjusted to about 10-12 with 2 N NaOH.

The D-GL solution was added to the insulin solution; the molar ratio of insulin to D-GL added to the reaction mixture was 10:1. The reaction was allowed to proceed for one hour at about 35° to 40° C. The reaction mixture was then dialyzed against 0.1 M (NH$_4$)$_2$CO$_3$ containing $2.5 \times 10^{-5}$ M EDTA and fractionated on a Sephadex 675 column using 0.01 M NH$_4$HCO$_3$, containing $2.5 \times 10^{-5}$ M EDTA as the eluant. The conjugate was further dialyzed against distilled water and lyophilized.

EXAMPLE IV

Nucleotide-D-GL Conjugate

Oligodeoxynucleotide (trimers and/or tetramers) were prepared by DNase 1 digestion of calf thymus DNA followed by fractionation on a DEAE Sephadex A25 column. The procedure involved using a 0–0.4 M LiCl linear gradient in 5 mM tris(hydroxymethyl)aminomethane ("TRIS") -7 M urea buffer (pH=7.6). Urea was removed from the oligodeoxynucleotides produced, by chromatographic techniques, using distilled water as the eluant.

The oligodeoxynucleotide produced is reacted with D-GL copolymer, having a average molecular weight of about 64,000 and a glutamic acid:lysine molar ratio of 60:40. The reaction is conducted in distilled water, using 1-ethyl-3-diisopropylaminocarbodiimide hydrochloride (EDC) as the coupling agent.

The resultant conjugate is separated from impurities and unreacted starting material by dialysis for about one week at about 2° to 4° C. [See *J. of Immun.*, 96, 373 (1966)].

Oligoneucleotides were also prepared by DNase 1 digestion of calf thymus DNA followed by passing the material through a filter having a molecular weight cut-off of about 10,000. A suitable filter is available from Amicon, division of Rohm and Haas Co., Independence Mall West, Philadelphia, Pennsylvania, 19105, under the trade designation PM-10. The filtrate was used as the source of the oligodeoxynucleotide.

Nucleotides are composed of a heterocyclic base, a five carbon sugar and phosphate. In turn, nucleic acids are polymers composed of four different nucleotides, linked together by phospho-diester bonds. Oligonucleotides are small polymers, usually obtained from nucleic acids, composed of fewer than 10 nucleotides which are linked together by phospho-diester bonds. The diester bonds make the nucleotides relatively complex chemical substances. Antibodies specific for nucleic acid are not only specific for the base and/or sugar but also for the phosphate backbone containing these nucleotides. Thus, by using a small oligonucleotide attached to a nonimmunogenic carrier (e.g., D GL), a nucleic acid-like environment directly related to the pathological state of an autoimmune disease is obtained. In contrast, prior art induction of tolerance to nucleosides, which do not contain phospho-diester bonds, is more closely related to hapten-D-GL tolerance, e.g., Dnp-D-GL. Induction of tolerance to oligodeoxynucleotides can be considered to be equivalent to induction of tolerance to nucleic acid.

EXAMPLE V

Ragweed Antigen E-D-GL Conjugate

A 50 mg portion of D-GL copolymer having an average molecular weight of 64,000 and a glutamic acid:lysine molar ratio of 60:40 was dissolved in 2 ml of distilled water. The solution was cooled to 0° C. in an ice bath and stirred. A 50 mg portion of N-ethyl-5-phenylisoxazolium 3'-sulfonate (Woodward's Reagent), was dissolved in 0.5 ml of distilled water, added to the D-GL solution and stirring continued for about 1 hour at 0° C. The pH was raised to 7.5–8.0 with 2 N NaOH.

A 5 mg portion of ragweed antigen E, available from Worthington Biochemicals, Inc., Freehold, New Jersey, 07728, was dissolved in distilled water and added to the D-GL-Woodward's Reagent solution. The antigen E had a molecular weight of 37,800; nitrogen was 17.1 percent and carbohydrate was 0.2 percent. The S value was 3.05 and the extinction coefficient (280μ) of a 1 percent solution at 1 cm was 11.3.

The mixture was stirred for 24 hours at 6° C. The reaction mixture was fractionated on a Sephadex G-100 column using 0.01 M $NH_4HCO_3$, containing 0.1 M $NH_4HCO_3$ as the eluant. The tubes containing the first peak were pooled together and the conjugate further dialyzed against distilled water and lyophilized.

The present invention has therapeutic implications for treatment of pathological manifestations involving any antibody dysfunction. Since, as indicated earlier, a large number of individuals are hypersensitive to environmental antigens, a method of treatment to alleviate these allergic symptoms would be of immense therapeutic value. By the present invention, IgE and IgG antibody production in response to specific sensitizing antigens is greatly suppressed.

Accordingly, the antigen-D-GL conjugate and treatment of the present invention includes a wide variety of environmental antigens, denoted as allergens. For example, representative allergens include, but are not limited to: drugs such as penicillin; hormones such as insulin; pollens such as ragweed, bermuda grass, orchard grass and timothy grass, flower pollen such as Chrysanthemum leucanthemum, and tree pollen such as birch; venoms such as bee wasp and snake; animal danders such as horse dander; animal epidermis such as cat epithelium; food protein allergens such as haddock, strawberries; house dust mite; fungi such as baker's yeast (Saccharomyces cerevisiae); molds such as Alternaria tenuis; toxins such as diphtheria; toxoids such as tetanus; proteins such as ovalbumin; enzymes such as trypsin, chymotrypsin and ficin; and derivatives of these allergens.

In addition to the environmental allergens described above, which produce allergic symptoms in hypersensitive individuals, the instant invention has therapeutic value for treatment of autoimmune disease. Autoimmune diseases can affect almost every part of an individual's body. Some responses are directed to organ-specific antibodies, and can be directed to a particular cell type, e.g., parietal cells of gastric mucosa in pernicious anemia. Other responses are directed to widely distributed antigens and are associated with disseminated diseases, e.g., antinuclear antibodies in systemic lupus erythematosus (SLE). In still other diseases, the responses are intermediate between these extremes, e.g., in Goodpasture's disease, characterized by chronic glomerulonephritis and pulmonary hemorrhages, antibodies are deposited on basement membrane of kidney glomeruli and lung parenchyma.

Antibodies are also formed to specific cell receptor sites as occurs in myasthenia gravis where antibodies to acetylcholine receptor sites interfere with the transmission of neural impulses. Antibodies can be formed to insulin receptor sites, blocking the binding of insulin to the cells, which interferes with the regulatory action of the hormone.

Representative autoimmune diseases, and the antigen responsible include:

| | | |
|---|---|---|
| Thyroid | Hashimoti's thyroiditis (hypothyroidism) Thyrotoxicosis (hyperthyroidism) | Thyroglobulin; and Thyroid cell surface; |
| Gastric factor(1) mucosa | Pernicious anemia (vitamin $B_{12}$ deficiency) | Parietal cells |
| Adrenals | Addison's disease | Adrenal cell |
| Skin | Pemphigus vulgaris Pemphigoid | Epidermal cells and Basement membrane between epidermis-dermis |
| Eye | Sympathetic ophthalmia | Uvea; |
| Red cells | Autoimmune hemolytic anemia | Red cell surface; |
| Platelets | Idiopathic thrombocytopenic purpura | Platelet surface; |
| Skeletal and heart muscle | Myasthenia gravis | Muscle cells and thymus "myoid" cells; |
| Liver (biliary tract) | Primary biliary cirrhosis | Mitochondria (mainly); |
| Salivary and lacrimal glands | Sjögren's disease | Includes secretory ducts, mitochondria, nuclei and IgG; |
| Synovial membranes, etc. | Rheumatoid arthritis | Fc domain of IgG |

By the method of the instant invention it appears that alleviation of autoimmune disease can be achieved by coupling to D-GL the appropriate antigen which has been implicated in the various autoimmune diseases referred to above. Suppression of formation of the IgG antibodies to the self-antigens would be of therapeutic value.

What is claimed is:

1. A therapeutic immunosuppressive agent capable of inducing specific immunological tolerance to an antigen by suppression of antibody response, comprising a conjugate of D-glutamic acid:D-lysine copolymer and the antigen benzylpenicilloyl.

2. An immunosuppressive agent as claimed in claim 1 wherein said copolymer has a molecular weight of from about 34,000 to 64,000 and a glutamic acid:lysine molar ratio of about 60:40.

3. A method of preparing a therapeutic immunosuppressive agent comprising a conjugate of D-glutamic acid:D-lysine copolymer and an antigen which is an allergen or a self-antigen, comprising the steps of reacting D-glutamic acid:D-lysine copolymer, having an average molecular weight of from about 34,000 to 64,000 and a glutamic acid:lysine molar ratio of about 60:40, with the antigen benzylpenicilloyl.

4. A method as claimed in claim 3 wherein the reaction mixture is maintained at a pH of about 10–12.

* * * * *